US00PP12273P2

(12) United States Plant Patent
Lemon

(10) Patent No.: US PP12,273 P2
(45) Date of Patent: Dec. 11, 2001

(54) VARIETY OF GERANIUM PLANT NAMED 'NATALIE'

(75) Inventor: David Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/745,094

(22) Filed: Dec. 20, 2000

(51) Int. Cl.[7] ..... A01H 5/00
(52) U.S. Cl. ..... Plt./329
(58) Field of Search ..... Plt./329, 325

(56) References Cited

U.S. PATENT DOCUMENTS

P.P. 11,253 * 2/2000 Hofmann ..... Plt./329

* cited by examiner

*Primary Examiner*—Amy J. Nelson
*Assistant Examiner*—Kent L. Bell
(74) *Attorney, Agent, or Firm*—Webb Ziensenheim Logsdon Orkin & Hanson, P.C.

(57) ABSTRACT

A new and distinct zonal geranium plant with pink-lavender colored flowers above medium green foliage with a dark reddish-brown zone. The plant flowers continuously throughout the year and is suitable for planting in containers or in the ground.

1 Drawing Sheet

BACKGROUND OF THE INVENTION

The present invention comprises a new and distinct cultivar of *Pelargonium×hortorum* known by the varietal name 'Natalie'. The new variety was discovered in a selected breeding program in Lompoc, Calif. The new variety is a selection from the cross of 'Gypsy Girl' (U.S. Plant Pat. No. 10,018), the female parent and 'Pinto Violet' (unpatented), the male parent. The new variety is very free flowering with similar flower type to 'Gypsy Girl' but is more compact than 'Gypsy Girl' with improved flower color and has semi-double flowers rather than the single flowers of 'Pinto Violet'. The new variety was first asexually reproduced by cuttings at Oglevee, Ltd. in Lompoc, Calif. The new variety has been trial and field tested at Connellsville and has been found to retain its distinctive characteristics and remain true to type through successive propagations.

The cutlivar, when grown in a glass greenhouse in Connellsville, Pa. using natural light and temperatures of 60° F. night and 68° F. day, has a response time of 5–6 weeks from a rooted cutting to a saleable product in a 4 inch pot. The response time was determined on plants grown in soilless media employing constant fertilizer 200–225 parts per million of nitrogen and potassium in full light.

DESCRIPTION OF THE DRAWINGS

The accompanying photographic drawing illustrates the new variety, with the color being as nearly true as is possible with the color illustrations of this type.

DESCRIPTION OF THE PLANT

The following detailed description sets forth the characteristics of the new cultivar. The data which defines these characteristics were collected by asexual reproductions carried out in Connellsville, Pa. The color readings were taken indoors under 200–220 foot candles of fluorescent cool white light. Color references are primarily to The R.H.S. Colour Chart of The Royal Horticultural Society of London. Plants described were about 5–6 weeks old from a rooted cutting.

PLANT

Classification:
*Botanical.*—*Pelargonium×hortorum.*
*Commercial.*—Zonal geranium.
Form: Semi-dwarf, uniform mound.
Height: 23–26 cm from media surface to top of foliage. 28–32 cm from media surface to top of umbels.
Growth: Free basal branching; lateral and procumbent habit.
Strength: Does not require artificial support.
Foliage: Light zoning; stalked leaf attachment.
Rooting time: 14–21 days depending on conditions.
Leaves:
*Size.*—Length: 6–8 cm. Width: 6–8 cm.
*Shape.*—Reniform; truncate base.
*Margin.*—Crenate; lobed.
*Texture.*—Pubescent.
*Color.*—Upper surface: Green Group 143A with zone of Green Group 187A. Lower surface: Green Group 138B.
*Ribs and veins.*—Venation: Palmate. Color: Yellow-Green Group 145A as seen from upper surface.
Petioles:
*Color.*—Yellow-Green Group 144A.
*Length.*—4–8 cm.
Stem/branches:
*Color.*—Yellow-Green Group 144A.
*Overall stem length.*—12–15 cm.
*Internode length.*—2.5–3.5 cm.
*Lateral branch length.*—12–15 cm.

THE BUD

Shape when just showing color:
*Overall.*—Elliptical cluster.
*Individual bud.*—Elliptical.
Size when just showing color:
*Overall.*—3.5–4 cm across.
*Individual bud.*—7–10 mm long.
Color: Yellow-Green Group 144A.

INFLORESCENCE

Blooming habit: Continuous; upright.

*Size.*—Width: 8–11 cm across fully open bloom. Depth: 8–11 cm.

*Borne.*—5–10 cm above foliage.

Flowers:

*Form.*—Slightly cupped; ruffled.

*Number of flowers per umbel.*—15–25.

*Size.*—2–2.5 cm long; 3–4 cm wide.

*Petals.*—Color: Upper surface: Outer edge: Red-Purple Group 68A fading to Red-Purple Group 68C in middle and Red-Purple Group 68D towards base of petal. Veining of Red-Purple Group 67B present on most petals. Lower surface: Red-Purple Group 68D. Shape: Curled; ruffled. Size: 18–20 mm long; 7–15 mm wide. Number per flower: 8–11.

*Texture and appearance.*—Smooth, velvety, reflective.

Petaloids:

*Quantity.*—2–5 per flower.

*Shape.*—Twisted; irregular; some tubular-like.

*Color.*—Same as petals.

Pedicel:

*Length.*—2–3 cm.

*Color.*—Yellow-Green Group 144A with Greyed-Purple Group 182B.

Peduncle:

*Length.*—12–16 cm.

*Color.*—Yellow-Green Group 144A with Greyed-Purple Group 183B.

Disease/pest resistance: No susceptibility to diseases or pests has been noted to date.

Lasting quality: Individual flowers and umbels will last from 7–14 days depending on conditions. Flowering is continuous with new replacing the old throughout the growing season.

Flowering season: Will flower through all seasons.

REPRODUCTIVE ORGANS

Stamens:

*Anthers.*—2 mm long.

*Filaments.*—Length: 5–6 mm. Color: White with pink tips. Pollen: Orange.

Pistils:

*Number.*—One.

*Length.*—7–8 cm.

*Stigma.*—Light pink in color.

*Style.*—Length: 3 mm. Color: Light pink.

Ovaries:

*Completeness.*—Superior.

*Pubescence.*—Very pubescent.

*Length.*—4–5 mm.

*Color.*—Green.

Fruit: None observed.

GENERAL CHARACTERISTICS

1. A mound of medium green foliage with a dark reddish-brown zone.
2. Striking pink-lavender flowers.
3. Many flower clusters create continuous bloom.
4. Good for containers or ground plantings.

I claim:

1. A new and distinct variety of geranium plant substantially as shown and described.

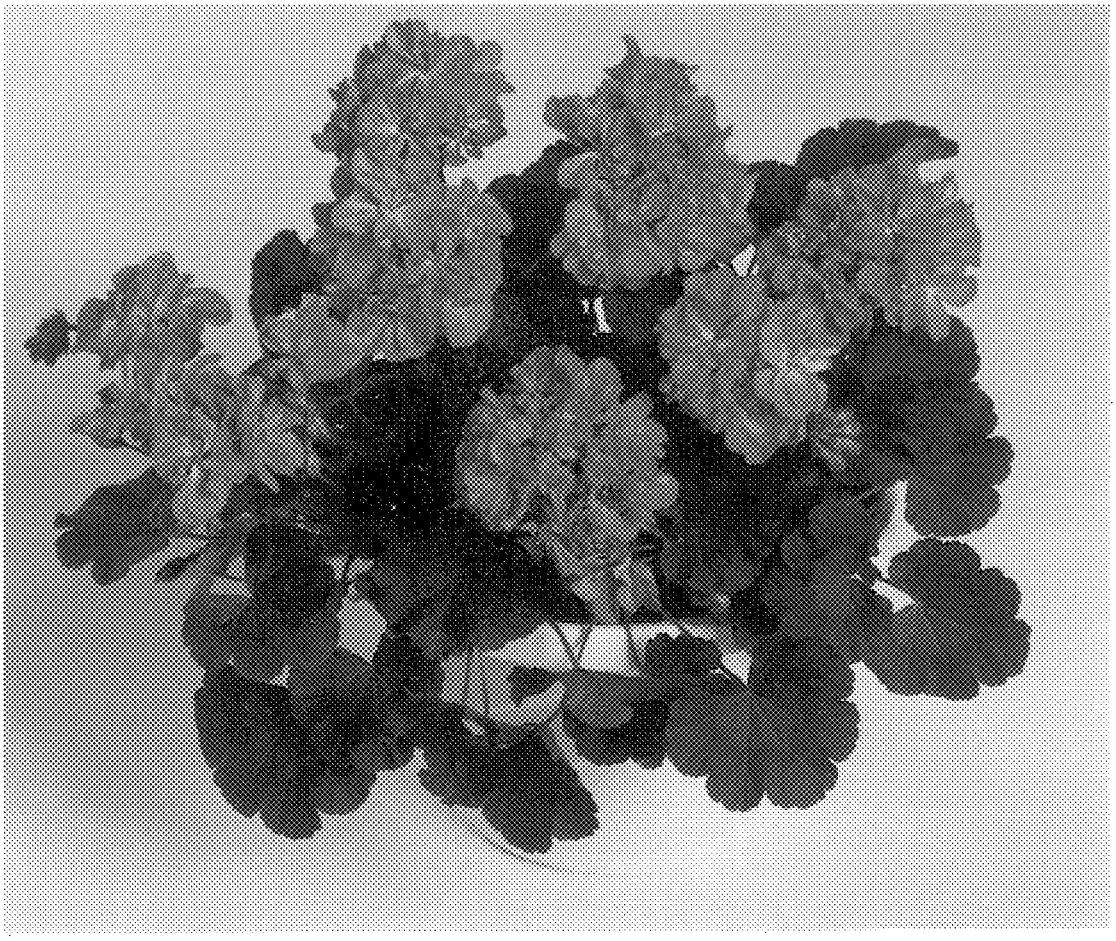

* * * * *